(12) United States Patent
Chen et al.

(10) Patent No.: US 7,465,792 B2
(45) Date of Patent: Dec. 16, 2008

(54) FUNGI NON-LTR RETROTRANSPOSONS AND METHODS RELATED THERETO

(75) Inventors: Yi-Pei Chen, Yingge Township, Taipei County (TW); Li-Ling Liaw, Hsinchu (TW); Chun-Lin Wang, Hsinchu (TW); Ching-Ping Tseng, Hsinchu (TW); Gwo-Fang Yuan, Hsinchu (TW)

(73) Assignee: Food Industry Research & Development Institute, Hsinchu (TW)

( * ) Notice: Subject to any disclaimer, the term of this patent is extended or adjusted under 35 U.S.C. 154(b) by 304 days.

(21) Appl. No.: 11/180,959

(22) Filed: Jul. 13, 2005

(65) Prior Publication Data

US 2006/0148088 A1    Jul. 6, 2006

(30) Foreign Application Priority Data

Dec. 31, 2004    (TW) .............................. 93141724 A

(51) Int. Cl.
  *C12N 15/11* (2006.01)
  *C12N 15/63* (2006.01)
  *C07K 14/00* (2006.01)
  *C12N 1/20* (2006.01)
(52) U.S. Cl. .................... 536/23.1; 530/350; 435/320.1
(58) Field of Classification Search ....................... None
See application file for complete search history.

(56) References Cited

U.S. PATENT DOCUMENTS

| 6,150,160 | A | 11/2000 | Kazazian et al. | ......... | 435/320.1 |
| 2004/0072325 | A1 * | 4/2004 | Anazawa et al. | ......... | 435/252.3 |

OTHER PUBLICATIONS

McHale et al. CfT-I: an LTR-retrotransposon in Cladosporium fulvum, a fungal pathogen of tomato. Mol. Gen. Genet. 233: 337-347, 1992.*
"Retrovirus-like Particles Contraining RNA Homologous to the Transposable Element *Copia* in *Drosophila melanogaster*" Shiba et al., Mar. 1983, pp. 119-124.
"Monacolin M, A New Inhibitor of Cholesterol Biosynthesis" Endo et al., Dec. 1986, pp. 1670-1673.
"The NeighboR-Joining Method: A New Method for Reconstructing Phylogenetic Trees" Saitou et al., 1987, pp. 406-425.
"Biosynthesis of Monacolins: Conversion of Monacolin J to Monacolin K (Mevinolin)" Kimura et al., May 1990, pp. 1621.
"Retroelements, Reverse Transcriptase and Evolution" Flavell, 1995, pp. 3-15.
"MAGGY, A Retrotransposon in the Genome of the Rice Blast Fungus *Magnaporthe grisea*" Farman et al., 1996, pp. 665-674.
"*Cg*T1: A Non-LTR Retrotransposon with Restricted Distribution in the Fungal Phytopathogen *Colletotrichum gloeosporioides*" He et al., 1996, pp. 320-331.
"Human L1 Retrotransposon Encodes a Conserved Endonuclease Required for Retrotransposition" Feng et al., Nov. 1996, pp. 905-916.
"The Bov-B Lines Found in *Vipera Ammodytes* Toxic $PLA_2$ Genes are Widespread in Snake Genomes" Kordis et al., 1998, pp. 1585-1590.
"Molecular Evolution of Bov-B Lines in Vertebrates" Kordis et al., 1999, pp. 171-178.
"The Age and Evolution of Non-LTR Retrotransposable Elements" Malik et al., 1999, pp. 793-805.
"Ketosynthesase Domain Probes Identify Two Subclasses of Fungal Polyketide Synthase Genes" Bingle et al., 1999, pp. 209-223.
"*REAL*, an LTR Retrotransposon from the Plant Pathogenic Fungus *Alternaria alternata*" Kaneko et al., 2000, pp. 625-634.
"*marY2N*, a Line-Like Non-Long Terminal Repeat (Non-LTR) Retroelement from the Ectomycorrhizal Homobasidiomycete *Tricholoma matsutake*" Murata et al., 2001, pp. 2301-2305.
"L1-like non-LTR Retrotransposons in the Yeast *Candida Albicans*" Goodwin et al., 2001, pp. 83-91.
"Pyret, a Ty3/Gypsy Retrotransposon in *Magnaporthe grisea* Contains an Extra Domain Between the Nucleocapsid and Protease Domains" Nakayashiki et al., 2001, pp. 4106-4113.
"Identification, Phylogeny, and Evolution of Retroviral Elements Based on Their Envelope Genes" Benit et al., 2001, pp. 11709-11719.
"Ylli, a Non-LTR Retrotransposon L1 Family in the Dimorphic Yeast *Yarrowia lipolytica*" Casaregola et al., 2002, pp. 664-676.
"*Nht2*, a *copia* LTR Retrotransposon from a Conditionally Dispensable Chromosome in *Nectria haematococca*" Shiflett et al., 2002, pp. 99-106.
"Transposable Elements in FilamentousFungi" Daboussi et al., Jun. 2003, pp. 275-299.

* cited by examiner

*Primary Examiner*—David Guzo
*Assistant Examiner*—Michele K. Joike
(74) *Attorney, Agent, or Firm*—Thomas, Kayden, Horstemeyer & Risley

(57) ABSTRACT

Retrotransposons and methods related thereto. The retrotransposon comprises a nucleotide sequence selected from a group consisting of a nucleotide sequence of SEQ ID NO: 1, a nucleotide sequence of SEQ ID NO: 2, a nucleotide sequence of SEQ ID NO: 3, and a nucleotide sequence encoding a polypeptide of an amino acid sequence of SEQ ID NO: 4.

12 Claims, 4 Drawing Sheets

(Probe 1)

A

| SEQ ID NO: 11 | MpT3 | <Y&RKD&P&H | PDITA&EVDG | LTI&N&YRPPND |
| --- | --- | --- | --- | --- |
| SEQ ID NO: 12 | MpT4 | <Y&RKD&P&H | PDITA&EVDG | LTI&N&YRPPND |
| SEQ ID NO: 13 | Zorro3 | <&GSKN&G&H | IDIWF&QEIR | FKIRDNDNHHTT |
| SEQ ID NO: 14 | L1Md | YF&&SLN&NGL | PTFCC&QETH | L&I&N&YAPNAR |
| SEQ ID NO: 15 | Ylli | QAK&KSPN&KVI | PD&VL&QETN | FTT&FEYFPALD |
| SEQ ID NO: 16 | Tadl | QLK&&YWN&GKS | YDIVA&QEPG | TT&YS&YSPILT |

| SEQ ID NO: 11 (continued) | MpT3 | NTIIAGDFNTHHPLWQ | &LCMEP&TPTR&PNTLDL&AN |
| --- | --- | --- | --- |
| SEQ ID NO: 12 (continued) | MpT4 | NTIIAGDFNTHHPLWQ | &LCMEP&TPTR&PNTLDL&AN |
| SEQ ID NO: 13 (continued) | Zorro3 | NIIY&GD&NHIM&LDD | &QPTNFH&NKSVKKRLDR&&D |
| SEQ ID NO: 14 (continued) | L1Md | HTIIVGDFNTPL&SKD | KGYTFFSAPHGTFSK&DH&IGH |
| SEQ ID NO: 15 (continued) | Ylli | PLIAAGD&NAVA&NDG | GLYTHTNNSRG&GRRLDQ&H&S |
| SEQ ID NO: 16 (continued) | Tadl | NL&AVGDLNLHHPDWD | PTRLGN&TRGERDGT&DHA&&S |

| SEQ ID NO: 11 (continued) | MpT3 | FSDHKTILAQLK& |
| --- | --- | --- |
| SEQ ID NO: 12 (continued) | MpT4 | FSDHKTILAQLK& |
| SEQ ID NO: 13 (continued) | Zorro3 | ISTHKIIA&SF&I |
| SEQ ID NO: 14 (continued) | L1Md | LSDHHG&R&IF&N |
| SEQ ID NO: 15 (continued) | Ylli | KSSHHA&QFVF&& |
| SEQ ID NO: 16 (continued) | Tadl | GSDHCPQE&WV&V |

FIG. 3A

B     YXDD

| SEQ ID NO: 17 | MpT3 | &VV&&YK&SFCYADDLG&LFVG-DSLQETSQ&L& |
| --- | --- | --- |
| SEQ ID NO: 18 | MpT4 | &VV&&YK&SFCYADDLG&LFVG-DSLQETSQ&L& |
| SEQ ID NO: 19 | Tadl-1 | &ATIPNTITV&&ADDTN&VAVA-RTTEENCRTLQ |
| SEQ ID NO: 20 | R2Dm | KVGN&ITNAA&&ADDLV&&AETRMGLQVL&DKT& |
| SEQ ID NO: 21 | R4 | AGY&FE&&HQFYMDDLK&&ARTPAMLDSQ&QV&S |
| SEQ ID NO: 22 | L1Md | Q&GKEE&KISLLADD&I&&ISDPKNSTRE&LNL& |
| SEQ ID NO: 23 | Ylli | AVA&GH&KVSA&ADD&A&&LNN-IQDVAT&GR&& |
| SEQ ID NO: 24 | Zorro3 | &NEV&S&&YT&YADD&I&&FKN-KNDQER&Q&L& |

| | | |
|---|---|---|
| SEQ ID NO: 25 | MpT3 | RVSWVPGHTGIAGNELADRLAKQGAA |
| SEQ ID NO: 26 | MpT4 | RVSWVPGHTGIAGNELADRLAKQGAA |
| SEQ ID NO: 27 | CgT1 | QTHWSPGHQGIKGNEEADILAKEGTT |
| SEQ ID NO: 28 | RNaseH | QEEWVKGHDGDPGNEMADFLAKKGAS |

| | | |
|---|---|---|
| SEQ ID NO: 29 | MpT3 | ATCSCKKLKTPVHFFCCP |
| SEQ ID NO: 30 | MpT4 | ATCSCKKLKTPVHFFCCP |
| SEQ ID NO: 31 | L1Md | CWRGCGERGTLLHCWVEC |
| SEQ ID NO: 32 | R2Dm | CRAGCDAPTTNHIMQKC |
| SEQ ID NO: 33 | R4 | CRCCHAAPTAEHITSAC |
| SEQ ID NO: 34 | TadI-1 | -CACGLEKTFAHIVLNC |
| SEQ ID NO: 35 | Ylli | CGLCDKAIIQDEHEHIFC |
| SEQ ID NO: 36 | Zorro3 | CQLCNTETDGIVHHIEEC |

SEQUENCE LISTING

<160> NUMBER OF SEQ ID NOS: 36

<210> SEQ ID NO 1
<211> LENGTH: 3526
<212> TYPE: DNA
<213> ORGANISM: Monascus pilosus BCRC38072

<400> SEQUENCE: 1

```
catcatcctg gtccaagagc cttggacaaa aatggcaaaa cacctcacaa aaacacaccc      60
aagatatcaa ctcttcagcc caaccacccg ctgggaaatc aggccccgaa ctctaacata     120
cgtacggaaa gaccttccag ctcacgcact tccacaacca tcctccccag acatcacggc     180
agtagaggta gatggcctca caattatcaa tgtctaccgc cccccaaatg actcagtgac     240
tccctcttca cccaccagat ctataatcca caccctactt caatacccctg tcccacggaa    300 caccatcatt gcaggagact caacaccca ccaccccta tggcaaccag aaacccaact       360
acatgccctc tctgcaggag ctacagctct tgtagaatgg ttagaaaccc aaggactagt     420
gctctgcatg gaaccaggca ctccaacccg cggacccaac accttggacc tagtctttgc     480
caacctccca gtggtggcta cagtggagga ccaccttagc acctttagtg accataaaac     540
tatcctagca cagctaaaat ggagggagcc acagccacaa cacaaactag gctccactaa     600
ctgggaaaag gctcgagaac tcctggtccc cccagacgct gacctaccaa cagatactct     660
ggcggaggaa ctggtcagcc gggtacagct agccatccag ggagcatcag agtataacac     720
ccgcaggctc ccacacaccc catggtggac accagagctc acaaacctac tccggcaagc     780
aagacaacat ccaccagacc tccaacctct tcagaaggca atttcaaagg caaaagccaa     840
ttactggaag gaacggattg agcaggcaac aactcccact aaagccttta cactagcaaa     900
atggcagaag ccctccaacc aactagcttc gccccccta cttgtacaag gcaaccaaat     960
caccacccca cagggcaaag cagatgcgtt cctcacccac ctcctgaaaa agggagtctc    1020
cctcccaaac cagctcgaag agggaccacc aaacagacct ttagatccta tgcctttacc    1080
aacaaaggaa gaatgctgga atacccttg ctcccctagc ccatctgccc ctggggagga    1140
cagccttacc acatctgtat ggagagaatt atggcctgtt ataggagatg cagttacagc    1200
attatatcat caaagcctag agaaaggcct tgtcccacag atctttaaag cagcaaaaat    1260
catcatgctg ccaaagccag gaaagagaga cctcacccaa cttggctcat ggcgacctat    1320
cagccttcta tccaccctag gcaaaggcct agaacgtctc attgcaagat ggatggctgt    1380
acaagcaatc cagggaaaac tactcacacc atgccacttt ggtgctctcc caggccgctc    1440
tgctattgac ctcgtccaag tactagttca tagagtggag aaagccttcc aacagggaaa    1500
ggtagcctca ttacttttga tggatgtaaa gggagccttt gacgcagtag accaccaaag    1560
gcttctttca cacctacgcc ttcagggatg ggatgaacgc ctgctccaat ggatccagga    1620
```

-continued

```
ctggctctcc agtcgctcag catgtgtcca gattggagag gcgaatgcca aagccccaat     1680
aaagggaggc ctcccacaag gatctcctct ctccccaatc cttttcctac tctatgcagc     1740
aatggtggta gctgcctata aggcctcctt ctgctacgcg gatgacctag gaatcctctt     1800
tgtaggggac tctctccagg agacatctca acagctagtg gaaacataca aggcagtaac     1860
agccctggga acagaggtag gtctcccttt ttctgctgag aaggcagaga tacaacactt     1920
ctctaggaaa cgcaagcatc cacccccagt ggttaggctg cctgatgtgg gtgagatccc     1980
tcccacatcg tacacccgct ggttaggggt cctcttggac ataaagctca cttttaaacc     2040
acatatcaac tgggtgttca gccgtggtaa gcagctggca caacacctac aaagactgag     2100
caacacccag cgtgggtgcc cagtagcctc tatgcgagca gctgtactac agtgcgcact     2160
accaacagca ttatatggag tggaggtctt ctatactgga caacagcagg tggctaactc     2220
ccttcagtcc ctgctccgca ttgccgcact agcaatcctc ccagcctaca agacaacacc     2280
cacagcagca ctcctccgag aggcagacct gccagaccca gagcctttc tggagagcat     2340 cctccagagg gcagctgcta gatatgcagg cctggatgca aagcaccctg tagcacgcat     2400
ccatgcagcc ccaaactatg ggtacaacac aaggctcacc aggatcctgc aacgcatccc     2460
cacaccagca ccagaacgca ggtgggtaga gccacagccc ccaccactac gcatgctgcc     2520
aacccaccgg gaagggcaca tctcctcacc actagccata tcagtctact cagatggctc     2580
ccacacgggc caaggcgctg gatatggata cgccatatac tacagctcca tcctagtcac     2640
ccagggacag ggcccagcag gccccggac agaggtctat gacgcggaga tcgtgggcgc     2700
tgtggaaggt ctccgggcag cagttggttt gccatgcacc gcatacgcca accagctgaa     2760
cctcttccta gacaacctgg cagcagccag tctactagca gatggcaggc ccgcgccaca     2820
cagacgccat ctcacagaca ccttccacca gctctccaag cagtggctca gcctgccgta     2880
catcctagcc tctccccgca ggcccgtacg ggtctcttgg gtaccagggc acactggaat     2940
cgcaggcaat gagctggcag acaggctagc aaagcaggga gcagccatgg agggctccca     3000
catccccccc tccccggcat acctgagacg agaggcgaaa caacaactcc atactgccac     3060
ccaggcagcg tatacgcgca gcgcaccca ggcataccaa gacctgggca tccgccccca     3120
tacgaagagc agccgggccc aggaacataa attaccacgc tgggtactag gcaggctcat     3180
tgcggcccgc actggacatg gggtcttcgc agcataccat gaacgcttcc accacactga     3240
ctacctagca acctgctcct gcaagaagct aaagaccca gtacatttct cttctgccc     3300 acatactagg aagcgctgga aggagagacg gaaacacaca ctagctgggc agcaaaaac     3360 cattgactgg ctcctaggga ctgctgctgg ggctgaggaa ttcatccgca tcgtgcaaaa     3420
cacatccttc tttacggata tatgcccaaa ctgggcccac ctaaacacag agtagtgtac     3480
agtcaacaca tatcttcctg ggaaagaggg actggctccc cctctc                   3526
```

<210> SEQ ID NO 2
<211> LENGTH: 1147
<212> TYPE: PRT
<213> ORGANISM: Monascus pilosus BCRC38072

<400> SEQUENCE: 2

Met Ala Lys His Leu Thr Lys Thr His Pro Arg Tyr Gln Leu Phe Ser
1               5                   10                  15

Pro Thr Thr Arg Trp Glu Ile Arg Pro Arg Thr Leu Thr Tyr Val Arg
            20                  25                  30

```
Lys Asp Leu Pro Ala His Ala Leu Pro Gln Pro Ser Ser Pro Asp Ile
        35                  40                  45

Thr Ala Val Glu Val Asp Gly Leu Thr Ile Ile Asn Val Tyr Arg Pro
 50                  55                  60

Pro Asn Asp Ser Val Thr Pro Ser Ser Pro Thr Arg Ser Ile Ile His
 65                  70                  75                  80

Thr Leu Leu Gln Tyr Pro Val Pro Arg Asn Thr Ile Ile Ala Gly Asp
                 85                  90                  95

Phe Asn Thr His His Pro Leu Trp Gln Pro Glu Thr Gln Leu His Ala
                100                 105                 110

Leu Ser Ala Gly Ala Thr Ala Leu Val Glu Trp Leu Glu Thr Gln Gly
            115                 120                 125

Leu Val Leu Cys Met Glu Pro Gly Thr Pro Thr Arg Gly Pro Asn Thr
        130                 135                 140

Leu Asp Leu Val Phe Ala Asn Leu Pro Val Val Ala Thr Val Glu Asp
145                 150                 155                 160

His Leu Ser Thr Phe Ser Asp His Lys Thr Ile Leu Ala Gln Leu Lys
                165                 170                 175

Trp Arg Glu Pro Gln Pro Gln His Lys Leu Gly Ser Thr Asn Trp Glu
                180                 185                 190

Lys Ala Arg Glu Leu Leu Val Pro Pro Asp Ala Asp Leu Pro Thr Asp
            195                 200                 205

Thr Leu Ala Glu Glu Leu Val Ser Arg Val Gln Leu Ala Ile Gln Gly
        210                 215                 220

Ala Ser Glu Tyr Asn Thr Arg Arg Leu Pro His Thr Pro Trp Trp Thr
225                 230                 235                 240

Pro Glu Leu Thr Asn Leu Leu Arg Gln Ala Arg Gln His Pro Pro Asp
                245                 250                 255

Leu Gln Pro Leu Gln Lys Ala Ile Ser Lys Ala Lys Ala Asn Tyr Trp
                260                 265                 270

Lys Glu Arg Ile Glu Gln Ala Thr Thr Pro Thr Lys Ala Phe Thr Leu
            275                 280                 285

Ala Lys Trp Gln Lys Pro Ser Asn Gln Leu Ala Ser Pro Pro Leu Leu
        290                 295                 300

Val Gln Gly Asn Gln Ile Thr Thr Pro Gln Gly Lys Ala Asp Ala Phe
305                 310                 315                 320

Leu Thr His Leu Leu Lys Lys Gly Val Ser Leu Pro Asn Gln Leu Glu
                325                 330                 335

Glu Gly Pro Pro Asn Arg Pro Leu Asp Pro Met Pro Leu Pro Thr Lys
                340                 345                 350

Glu Glu Cys Trp Asn Thr Leu Cys Ser Pro Ser Pro Ser Ala Pro Gly
            355                 360                 365

Glu Asp Ser Leu Thr Thr Ser Val Trp Arg Glu Leu Trp Pro Val Ile
370                 375                 380

Gly Asp Ala Val Thr Ala Leu Tyr His Gln Ser Leu Glu Lys Gly Leu
385                 390                 395                 400

Val Pro Gln Ile Phe Lys Ala Ala Lys Ile Ile Met Leu Pro Lys Pro
                405                 410                 415

Gly Lys Arg Asp Leu Thr Gln Leu Gly Ser Trp Arg Pro Ile Ser Leu
            420                 425                 430

Leu Ser Thr Leu Gly Lys Gly Leu Glu Arg Leu Ile Ala Arg Trp Met
        435                 440                 445

Ala Val Gln Ala Ile Gln Gly Lys Leu Leu Thr Pro Cys His Phe Gly
```

```
                450                 455                 460
Ala Leu Pro Gly Arg Ser Ala Ile Asp Leu Val Gln Val Leu Val His
465                 470                 475                 480

Arg Val Glu Lys Ala Phe Gln Gln Gly Lys Val Ala Ser Leu Leu Leu
                485                 490                 495

Met Asp Val Lys Gly Ala Phe Asp Ala Val Asp His Gln Arg Leu Leu
                500                 505                 510

Ser His Leu Arg Leu Gln Gly Trp Asp Glu Arg Leu Leu Gln Trp Ile
                515                 520                 525

Gln Asp Trp Leu Ser Ser Arg Ser Ala Cys Val Gln Ile Gly Glu Ala
530                 535                 540

Asn Ala Lys Ala Pro Ile Lys Gly Gly Leu Pro Gln Gly Ser Pro Leu
545                 550                 555                 560

Ser Pro Ile Leu Phe Leu Leu Tyr Ala Ala Met Val Val Ala Ala Tyr
                565                 570                 575

Lys Ala Ser Phe Cys Tyr Ala Asp Asp Leu Gly Ile Leu Phe Val Gly
                580                 585                 590

Asp Ser Leu Gln Glu Thr Ser Gln Gln Leu Val Glu Thr Tyr Lys Ala
                595                 600                 605

Val Thr Ala Leu Gly Thr Glu Val Gly Leu Pro Phe Ser Ala Glu Lys
                610                 615                 620

Ala Glu Ile Gln His Phe Ser Arg Lys Arg Lys His Pro Pro Pro Val
625                 630                 635                 640

Val Arg Leu Pro Asp Val Gly Glu Ile Pro Thr Ser Tyr Thr Arg
                645                 650                 655

Trp Leu Gly Val Leu Leu Asp Ile Lys Leu Thr Phe Lys Pro His Ile
                660                 665                 670

Asn Trp Val Phe Ser Arg Gly Lys Gln Leu Ala Gln His Leu Gln Arg
                675                 680                 685

Leu Ser Asn Thr Gln Arg Gly Cys Pro Val Ala Ser Met Arg Ala Ala
                690                 695                 700

Val Leu Gln Cys Ala Leu Pro Thr Ala Leu Tyr Gly Val Glu Val Phe
705                 710                 715                 720

Tyr Thr Gly Gln Gln Gln Val Ala Asn Ser Leu Gln Ser Leu Leu Arg
                725                 730                 735

Ile Ala Ala Leu Ala Ile Leu Pro Ala Tyr Lys Thr Thr Pro Thr Ala
                740                 745                 750

Ala Leu Leu Arg Glu Ala Asp Leu Pro Asp Pro Arg Ala Phe Leu Glu
                755                 760                 765

Ser Ile Leu Gln Arg Ala Ala Arg Tyr Ala Gly Leu Asp Ala Lys
770                 775                 780

His Pro Val Ala Arg Ile His Ala Ala Pro Asn Tyr Gly Tyr Asn Thr
785                 790                 795                 800

Arg Leu Thr Arg Ile Leu Gln Arg Ile Pro Thr Pro Ala Pro Glu Arg
                805                 810                 815

Arg Trp Val Glu Pro Gln Pro Pro Leu Arg Met Leu Pro Thr His
                820                 825                 830

Arg Glu Gly His Ile Ser Ser Pro Leu Ala Ile Ser Val Tyr Ser Asp
                835                 840                 845

Gly Ser His Thr Gly Gln Gly Ala Gly Tyr Gly Tyr Ala Ile Tyr Tyr
                850                 855                 860

Ser Ser Ile Leu Val Thr Gln Gly Gln Gly Pro Ala Gly Pro Arg Thr
865                 870                 875                 880
```

Glu Val Tyr Asp Ala Glu Ile Val Gly Ala Val Glu Gly Leu Arg Ala
            885                 890                 895

Ala Val Gly Leu Pro Cys Thr Ala Tyr Ala Asn Gln Leu Asn Leu Phe
        900                 905                 910

Leu Asp Asn Leu Ala Ala Ala Ser Leu Leu Ala Asp Gly Arg Pro Ala
        915                 920                 925

Pro His Arg Arg His Leu Thr Asp Thr Phe His Gln Leu Ser Lys Gln
        930                 935                 940

Trp Leu Ser Leu Pro Tyr Ile Leu Ala Ser Pro Arg Arg Pro Val Arg
945                 950                 955                 960

Val Ser Trp Val Pro Gly His Thr Gly Ile Ala Gly Asn Glu Leu Ala
            965                 970                 975

Asp Arg Leu Ala Lys Gln Gly Ala Ala Met Glu Gly Ser His Ile Pro
        980                 985                 990

Pro Ser Pro Ala Tyr Leu Arg Arg Glu Ala Lys Gln Gln Leu His Thr
        995                 1000                1005

Ala Thr Gln Ala Ala Tyr Thr Arg Ser Ala Pro Gln Ala Tyr Gln
    1010                1015                1020

Asp Leu Gly Ile Arg Pro His Thr Lys Ser Ser Arg Ala Gln Glu
    1025                1030                1035

His Lys Leu Pro Arg Trp Val Leu Gly Arg Leu Ile Ala Ala Arg
    1040                1045                1050

Thr Gly His Gly Val Phe Ala Ala Tyr His Glu Arg Phe His His
    1055                1060                1065

Thr Asp Tyr Leu Ala Thr Cys Ser Cys Lys Lys Leu Lys Thr Pro
    1070                1075                1080

Val His Phe Phe Phe Cys Pro His Thr Arg Lys Arg Trp Lys Glu
    1085                1090                1095

Arg Arg Lys His Thr Leu Ala Gly Pro Ala Lys Thr Ile Asp Trp
    1100                1105                1110

Leu Leu Gly Thr Ala Ala Gly Ala Glu Glu Phe Ile Arg Ile Val
    1115                1120                1125

Gln Asn Thr Ser Phe Phe Thr Asp Ile Cys Pro Asn Trp Ala His
    1130                1135                1140

Leu Asn Thr Glu
    1145

<210> SEQ ID NO 3
<211> LENGTH: 3530
<212> TYPE: DNA
<213> ORGANISM: Monascus pilosus BCRC31502

<400> SEQUENCE: 3
catcatcctg gtccaagagc cttggacaaa aatggcaaaa cacctcacaa aaacacaccc      60
aagatatcaa ctcttcagcc caaccaccaccg ctgggaaatc aggccccgaa ctctaacata     120
cgtacggaaa gaccttccag ctcacgcact ccacaaccaa tcctcccag acatcacggc      180 agtagaggta gatggcctca caattatcaa tgtctaccgc cccccaaatg actcagtgac     240
tccctcttca cccaccagat ctacaatcca caccctactt caataccctg tcccacggaa     300
caccatcatt gcaggagact tcaacaccca ccaccccta tggcaaccag aaacccaact      360
acatgccctc tctgcaggag ctacagctct tgtagaatgg ttagaaaccc aaggactagt     420
gctctgcatg gaaccaggca ctccaacccg cggacccaac accttggacc tagtctttgc     480

```
caacctccca gtggtggcta cagtggagga ccaccttagc acctttagtg accataaaac      540
tatcctagca cagctaaaat ggagggagcc acagccacaa cacaaactag gctccactaa      600
ctgggaaaag gctcgagaac tcctggtccc cccagacgct gacctaccaa cagatactct      660
ggcggaggaa ctggtcagcc gggtacagct agccatccag ggagcatcag agtataacac      720
ccgcaggctc ccacacaccc catggtggac accagagctc acaaacctac tccggcaagc      780
aagacaacat ccaccagacc tccaacctct tcagaaggca atttcaaagg caaaagccaa      840
ttactggaag gaacggattg agcaggcaac aactcccact aaagccttta cactagcaaa      900
atggcagaag ccctccaacc aactagcttc gccccccta cttgtacagg gcaaccaaat       960
caccacccca cagggcaaag cagatgcgtt cctcacccac ctcctgaaaa agggagtctc     1020
cctcccaaac cagctcgaag agggaccacc aaacagacct ttagatccta tgcctttacc     1080
aacaaaggaa gaatgctgga atacccttg ctcccctagc ccatctgccc ctggggagga     1140
cagccttacc acatctgtat ggagagaatt atggcctgtt ataggagatg cagttacagc     1200
attatatcat caaagcctag agaaaggcct tgtcccacag atctttaaag cagcaaaaat     1260
catcatgctg ccaaagccag aaagagaga cctcacccaa cttggctcat ggcgacctat      1320
cagccttcta tccaccctag gcaaaggcct agaacgtctc attgcaagat ggatggctgt     1380
acaagcaatc cagggaaaac tactcacacc atgccacttt ggtgctctcc caggccgctc     1440
tgctattgac ctcgtccaag tactagttca tagagtggag aaagccttcc aacagggaaa     1500
ggtagcctca ttacttttga tggatgtaaa gggagccttt gacgcagtag accaccaaag     1560
gcttctttca cacctacgcc ttcagggatg ggatgaacgc ctgctccaat ggatccagga     1620
ctggctctcc agtcgctcag catgtgtcca gattggagag gcaaatgcca agcccaat      1680 aaagggaggc ctcccacaag gatctcctct ctccccaatc cttttcctac tctatgcagc     1740
aatggtggta gctgcctata aggcctcctt ctgctacgcg gatgacctag gaatcctctt     1800
tgtaggggac tctctccagg agacatctca acagctagtg gaaacataca aggcagtaac     1860
agccctggga acagaggtag gtctcccttt ttctgcggag aagacagaga tacaacactt     1920
ctctaggaaa cgcaagcatc cacccccagt ggttaggctg cctgatgtgg gtgagatccc     1980
tcccacatca tacacccgct ggttagggt cctcttggac ataaagctca cttttaaacc      2040
acatatcaac tgggtgttca gccgtggtaa gcagctggca caacacctac aaagactgag     2100
caacacccag cgtgggtgcc cagtagcctc tatgcgagca gctgtactac agtgcgcact     2160
accaacagca ttatatggag tggaggtctt ctatactgga caacagcagg tggctaactc     2220
ccttcagtcc ctgctccgca ttgccgcact agcaatcctc ccagcctaca agacaacacc     2280
cacagcagca ctcctccgag aggcagacct gccagaccca agagcctttc tggagagcat     2340
cctccagagg gcagctgcta gatatgcagg cctagatgca aagcaccctg tagcacgcat     2400
ccatgcagcc ccaaactatg ggtacaacac aaggctcacc aggatcctgc aacgcatccc     2460
cacaccagca ccagaacgca ggtgggtaga gccacagccc ccaccactac gcatgctgcc     2520
aacccaccgg gaagggcaca tctcctcacc actagccata tcagtctact cagatggctc     2580
ccacacgggc caaggcgctg atatggata cgccatatac tacggctcca tcctagtcac     2640
ccagggacag ggcccagcag gccccagac agaggtttat gacgcggaga tcatgggcgc     2700
tgtggaaggt ctccgggcag cagttggttt gccatgcacc gcatacgcca accagctgaa     2760
cctcttccta gacaacctgg cagcagccag tctactagca gatggcaggc ccgcgccaca     2820
cagacgccat ctcacagaca ccttccacca gctctccaag cagtggctca gcctgccgta     2880
```

-continued

```
catcctagcc tctccccgca ggcccgtacg ggtctcttgg gtaccagggc acactggaat    2940
cgcaggcaat gagctggcag acaggctagc aaagcaggga gcagccatgg atggctccca    3000
catccccccc tccccggcat acctgagacg agaggcgaaa cagcaactcc atactgccac    3060
ccaggcagcg tatacgcgca gcgcacccca ggcataccaa gacctgggca tccgccccca    3120
tacgaagagc agccgggccc aggaacataa attaccacgc tgggtactag gcaggctcat    3180
tgcggcccgc actggacatg gggactttgc agcataccat gaacgcttcc accacactga    3240
ctacctagca acctgctcct gcaagaagct aaagaccccca gtacatttct tcttctgccc    3300
acatactagg aagcgctgga aggagagacg gaaacacaca ctagctgggc cagcaaaaac    3360
cattgactgg ctcctaggga ctgctgctgg ggctgaggaa ttcagccgca tcgtgcaaaa    3420
cacatccttc tttacggata tatgcccaaa ctgggcccac ctaaacacag agtagtgtac    3480
agtcaacaca tatcttcctg ggaaagaggg actggctccc cctctcacct              3530
```

<210> SEQ ID NO 4
<211> LENGTH: 1147
<212> TYPE: PRT
<213> ORGANISM: Monascus pilosus BCRC31502

<400> SEQUENCE: 4

```
Met Ala Lys His Leu Thr Lys Thr His Pro Arg Tyr Gln Leu Phe Ser
 1               5                  10                  15

Pro Thr Thr Arg Trp Glu Ile Arg Pro Arg Thr Leu Thr Tyr Val Arg
                20                  25                  30

Lys Asp Leu Pro Ala His Ala Leu Pro Gln Pro Ser Ser Pro Asp Ile
            35                  40                  45

Thr Ala Val Glu Val Asp Gly Leu Thr Ile Ile Asn Val Tyr Arg Pro
        50                  55                  60

Pro Asn Asp Ser Val Thr Pro Ser Ser Pro Thr Arg Ser Thr Ile His
    65                  70                  75                  80

Thr Leu Leu Gln Tyr Pro Val Pro Arg Asn Thr Ile Ile Ala Gly Asp
                85                  90                  95

Phe Asn Thr His His Pro Leu Trp Gln Pro Glu Thr Gln Leu His Ala
            100                 105                 110

Leu Ser Ala Gly Ala Thr Ala Leu Val Glu Trp Leu Glu Thr Gln Gly
        115                 120                 125

Leu Val Leu Cys Met Glu Pro Gly Thr Pro Thr Arg Gly Pro Asn Thr
    130                 135                 140

Leu Asp Leu Val Phe Ala Asn Leu Pro Val Val Ala Thr Val Glu Asp
145                 150                 155                 160

His Leu Ser Thr Phe Ser Asp His Lys Thr Ile Leu Ala Gln Leu Lys
                165                 170                 175

Trp Arg Glu Pro Gln Pro Gln His Lys Leu Gly Ser Thr Asn Trp Glu
            180                 185                 190

Lys Ala Arg Glu Leu Leu Val Pro Pro Asp Ala Asp Leu Pro Thr Asp
        195                 200                 205

Thr Leu Ala Glu Glu Leu Val Ser Arg Val Gln Leu Ala Ile Gln Gly
    210                 215                 220

Ala Ser Glu Tyr Asn Thr Arg Arg Leu Pro His Thr Pro Trp Trp Thr
225                 230                 235                 240

Pro Glu Leu Thr Asn Leu Leu Arg Gln Ala Arg Gln His Pro Pro Asp
                245                 250                 255
```

```
Leu Gln Pro Leu Gln Lys Ala Ile Ser Lys Ala Lys Ala Asn Tyr Trp
            260                 265                 270
Lys Glu Arg Ile Glu Gln Ala Thr Thr Pro Thr Lys Ala Phe Thr Leu
            275                 280                 285
Ala Lys Trp Gln Lys Pro Ser Asn Gln Leu Ala Ser Pro Pro Leu Leu
            290                 295                 300
Val Gln Gly Asn Gln Ile Thr Thr Pro Gln Gly Lys Ala Asp Ala Phe
305                 310                 315                 320
Leu Thr His Leu Leu Lys Lys Gly Val Ser Leu Pro Asn Gln Leu Glu
                325                 330                 335
Glu Gly Pro Pro Asn Arg Pro Leu Asp Pro Met Pro Leu Pro Thr Lys
            340                 345                 350
Glu Glu Cys Trp Asn Thr Leu Cys Ser Pro Ser Pro Ser Ala Pro Gly
            355                 360                 365
Glu Asp Ser Leu Thr Thr Ser Val Trp Arg Glu Leu Trp Pro Val Ile
            370                 375                 380
Gly Asp Ala Val Thr Ala Leu Tyr His Gln Ser Leu Glu Lys Gly Leu
385                 390                 395                 400
Val Pro Gln Ile Phe Lys Ala Ala Lys Ile Ile Met Leu Pro Lys Pro
                405                 410                 415
Gly Lys Arg Asp Leu Thr Gln Leu Gly Ser Trp Arg Pro Ile Ser Leu
            420                 425                 430
Leu Ser Thr Leu Gly Lys Gly Leu Glu Arg Leu Ile Ala Arg Trp Met
            435                 440                 445
Ala Val Gln Ala Ile Gln Gly Lys Leu Leu Thr Pro Cys His Phe Gly
            450                 455                 460
Ala Leu Pro Gly Arg Ser Ala Ile Asp Leu Val Gln Val Leu His
465                 470                 475                 480
Arg Val Glu Lys Ala Phe Gln Gln Gly Lys Val Ala Ser Leu Leu
            485                 490                 495
Met Asp Val Lys Gly Ala Phe Asp Ala Val Asp His Gln Arg Leu Leu
            500                 505                 510
Ser His Leu Arg Leu Gln Gly Trp Asp Glu Arg Leu Leu Gln Trp Ile
            515                 520                 525
Gln Asp Trp Leu Ser Ser Arg Ser Ala Cys Val Gln Ile Gly Glu Ala
            530                 535                 540
Asn Ala Lys Ala Pro Ile Lys Gly Gly Leu Pro Gln Gly Ser Pro Leu
545                 550                 555                 560
Ser Pro Ile Leu Phe Leu Leu Tyr Ala Ala Met Val Val Ala Ala Tyr
                565                 570                 575
Lys Ala Ser Phe Cys Tyr Ala Asp Leu Gly Ile Leu Phe Val Gly
            580                 585                 590
Asp Ser Leu Gln Glu Thr Ser Gln Gln Leu Val Glu Thr Tyr Lys Ala
            595                 600                 605
Val Thr Ala Leu Gly Thr Glu Val Gly Leu Pro Phe Ser Ala Glu Lys
            610                 615                 620
Thr Glu Ile Gln His Phe Ser Arg Lys Arg His Pro Pro Val
625                 630                 635                 640
Val Arg Leu Pro Asp Val Gly Glu Ile Pro Thr Ser Tyr Thr Arg
            645                 650                 655
Trp Leu Gly Val Leu Leu Asp Ile Lys Leu Thr Phe Lys Pro His Ile
            660                 665                 670
Asn Trp Val Phe Ser Arg Gly Lys Gln Leu Ala Gln His Leu Gln Arg
```

-continued

```
              675                 680                 685
Leu Ser Asn Thr Gln Arg Gly Cys Pro Val Ala Ser Met Arg Ala Ala
        690                 695                 700
Val Leu Gln Cys Ala Leu Pro Thr Ala Leu Tyr Gly Val Glu Val Phe
705                 710                 715                 720
Tyr Thr Gly Gln Gln Gln Val Ala Asn Ser Leu Gln Ser Leu Leu Arg
                725                 730                 735
Ile Ala Ala Leu Ala Ile Leu Pro Ala Tyr Lys Thr Thr Pro Thr Ala
                    740                 745                 750
Ala Leu Leu Arg Glu Ala Asp Leu Pro Asp Pro Arg Ala Phe Leu Glu
            755                 760                 765
Ser Ile Leu Gln Arg Ala Ala Arg Tyr Ala Gly Leu Asp Ala Lys
        770                 775                 780
His Pro Val Ala Arg Ile His Ala Ala Pro Asn Tyr Gly Tyr Asn Thr
785                 790                 795                 800
Arg Leu Thr Arg Ile Leu Gln Arg Ile Pro Thr Pro Ala Pro Glu Arg
                805                 810                 815
Arg Trp Val Glu Pro Gln Pro Pro Leu Arg Met Leu Pro Thr His
            820                 825                 830
Arg Glu Gly His Ile Ser Ser Pro Leu Ala Ile Ser Val Tyr Ser Asp
                835                 840                 845
Gly Ser His Thr Gly Gln Gly Ala Gly Tyr Gly Tyr Ala Ile Tyr Tyr
        850                 855                 860
Gly Ser Ile Leu Val Thr Gln Gly Gln Gly Pro Ala Gly Pro Gln Thr
865                 870                 875                 880
Glu Val Tyr Asp Ala Glu Ile Met Gly Ala Val Glu Gly Leu Arg Ala
                885                 890                 895
Ala Val Gly Leu Pro Cys Thr Ala Tyr Ala Asn Gln Leu Asn Leu Phe
            900                 905                 910
Leu Asp Asn Leu Ala Ala Ala Ser Leu Leu Ala Asp Gly Arg Pro Ala
        915                 920                 925
Pro His Arg Arg His Leu Thr Asp Thr Phe His Gln Leu Ser Lys Gln
    930                 935                 940
Trp Leu Ser Leu Pro Tyr Ile Leu Ala Ser Pro Arg Arg Pro Val Arg
945                 950                 955                 960
Val Ser Trp Val Pro Gly His Thr Gly Ile Ala Gly Asn Glu Leu Ala
                965                 970                 975
Asp Arg Leu Ala Lys Gln Gly Ala Ala Met Asp Gly Ser His Ile Pro
            980                 985                 990
Pro Ser Pro Ala Tyr Leu Arg Arg Glu Ala Lys Gln Gln Leu His Thr
        995                 1000                1005
Ala Thr Gln Ala Ala Tyr Thr Arg Ser Ala Pro Gln Ala Tyr Gln
    1010                1015                1020
Asp Leu Gly Ile Arg Pro His Thr Lys Ser Ser Arg Ala Gln Glu
    1025                1030                1035
His Lys Leu Pro Arg Trp Val Leu Gly Arg Leu Ile Ala Ala Arg
    1040                1045                1050
Thr Gly His Gly Asp Phe Ala Ala Tyr His Glu Arg Phe His His
    1055                1060                1065
Thr Asp Tyr Leu Ala Thr Cys Ser Cys Lys Lys Leu Lys Thr Pro
    1070                1075                1080
Val His Phe Phe Cys Pro His Thr Arg Lys Arg Trp Lys Glu
    1085                1090                1095
```

-continued

Arg Arg Lys His Thr Leu Ala Gly Pro Ala Lys Thr Ile Asp Trp
    1100            1105                1110

Leu Leu Gly Thr Ala Ala Gly Ala Glu Glu Phe Ser Arg Ile Val
    1115            1120                1125

Gln Asn Thr Ser Phe Phe Thr Asp Ile Cys Pro Asn Trp Ala His
    1130            1135                1140

Leu Asn Thr Glu
    1145

<210> SEQ ID NO 5
<211> LENGTH: 22
<212> TYPE: DNA
<213> ORGANISM: Artificial Sequence
<220> FEATURE:
<223> OTHER INFORMATION: primer sequence

<400> SEQUENCE: 5 gggggggaagc taggatatac gg                                          22

<210> SEQ ID NO 6
<211> LENGTH: 20
<212> TYPE: DNA
<213> ORGANISM: Artificial Sequence
<220> FEATURE:
<223> OTHER INFORMATION: primer sequence

<400> SEQUENCE: 6
gcaggtgggt agagccacag                                              20

<210> SEQ ID NO 7
<211> LENGTH: 21
<212> TYPE: DNA
<213> ORGANISM: Artificial Sequence
<220> FEATURE:
<223> OTHER INFORMATION: primer sequence

<400> SEQUENCE: 7
catcatcctg gtccaagagc c                                            21

<210> SEQ ID NO 8
<211> LENGTH: 20
<212> TYPE: DNA
<213> ORGANISM: Artificial Sequence
<220> FEATURE:
<223> OTHER INFORMATION: primer sequence

<400> SEQUENCE: 8
aggtgagagg gggagccagt                                              20

<210> SEQ ID NO 9
<211> LENGTH: 20
<212> TYPE: DNA
<213> ORGANISM: Artificial Sequence
<220> FEATURE:
<223> OTHER INFORMATION: primer sequence

<400> SEQUENCE: 9
acgaggcatc aatccatctc                                              20

<210> SEQ ID NO 10
<211> LENGTH: 20
<212> TYPE: DNA
<213> ORGANISM: Artificial Sequence
<220> FEATURE:

-continued

<223> OTHER INFORMATION: primer sequence

<400> SEQUENCE: 10
cgtgggtgct gtcatacttg                                           20

<210> SEQ ID NO 11
<211> LENGTH: 85
<212> TYPE: PRT
<213> ORGANISM: Monascus pilosus BCRC38072

<400> SEQUENCE: 11

Thr Leu Thr Tyr Val Arg Lys Asp Leu Pro Ala His Pro Asp Ile Thr
1               5                   10                  15

Ala Val Glu Val Asp Gly Leu Thr Ile Ile Asn Val Tyr Arg Pro Pro
            20                  25                  30

Asn Asp Asn Thr Ile Ile Ala Gly Asp Phe Asn Thr His His Pro Leu
        35                  40                  45

Trp Gln Val Leu Cys Met Glu Pro Gly Thr Pro Thr Arg Gly Pro Asn
    50                  55                  60

Thr Leu Asp Leu Val Phe Ala Asn Phe Ser Asp His Lys Thr Ile Leu
65                  70                  75                  80

Ala Gln Leu Lys Trp
            85

<210> SEQ ID NO 12
<211> LENGTH: 85
<212> TYPE: PRT
<213> ORGANISM: Monascus pilosus BCRC31502

<400> SEQUENCE: 12

Thr Leu Thr Tyr Val Arg Lys Asp Leu Pro Ala His Pro Asp Ile Thr
1               5                   10                  15

Ala Val Glu Val Asp Gly Leu Thr Ile Ile Asn Val Tyr Arg Pro Pro
            20                  25                  30

Asn Asp Asn Thr Ile Ile Ala Gly Asp Phe Asn Thr His His Pro Leu
        35                  40                  45

Trp Gln Val Leu Cys Met Glu Pro Gly Thr Pro Thr Arg Gly Pro Asn
    50                  55                  60

Thr Leu Asp Leu Val Phe Ala Asn Phe Ser Asp His Lys Thr Ile Leu
65                  70                  75                  80

Ala Gln Leu Lys Trp
            85

<210> SEQ ID NO 13
<211> LENGTH: 85
<212> TYPE: PRT
<213> ORGANISM: C. albicans

<400> SEQUENCE: 13

Ser Leu Thr Ile Gly Ser Lys Asn Ile Gly Ser His Ile Asp Ile Trp
1               5                   10                  15

Phe Ile Gln Glu Ile Arg Phe Lys Ile Arg Asp Asn Asp Asn His His
            20                  25                  30

Thr Thr Asn Ile Ile Tyr Gly Gly Asp Tyr Asn His Ile Met Ser Leu
        35                  40                  45

Asp Asp Leu Gln Pro Thr Asn Phe His Ser Asn Lys Ser Val Lys Lys
    50                  55                  60

Arg Leu Asp Arg Ile Tyr Ile Asp Ile Ser Thr His Lys Ile Ile Ala

```
                65                  70                  75                  80

Met Ser Phe Gln Ile
                85

<210> SEQ ID NO 14
<211> LENGTH: 85
<212> TYPE: PRT
<213> ORGANISM: mouse L1

<400> SEQUENCE: 14

Tyr Phe Ser Leu Ile Ser Leu Asn Ile Asn Gly Leu Pro Thr Phe Cys
1               5                   10                  15

Cys Leu Gln Glu Thr His Leu Ser Ile Leu Asn Ile Tyr Ala Pro Asn
            20                  25                  30

Ala Arg His Thr Ile Ile Val Gly Asp Phe Asn Thr Pro Leu Ser Ser
        35                  40                  45

Lys Asp Lys Gly Tyr Thr Phe Phe Ser Ala Pro His Gly Thr Phe Ser
    50                  55                  60

Lys Ile Asp His Ile Ile Gly His Leu Ser Asp His His Gly Leu Arg
65                  70                  75                  80

Leu Ile Phe Asn Asn
                85

<210> SEQ ID NO 15
<211> LENGTH: 85
<212> TYPE: PRT
<213> ORGANISM: Y. lipolytica

<400> SEQUENCE: 15

Gln Ala Lys Met Lys Ser Pro Asn Val Lys Val Ile Pro Asp Leu Val
1               5                   10                  15

Leu Leu Gln Glu Thr Asn Phe Thr Thr Val Phe Glu Tyr Phe Pro Ala
            20                  25                  30

Leu Asp Pro Leu Ile Ala Ala Gly Asp Trp Asn Ala Val Ala Ser Asn
        35                  40                  45

Asp Gly Gly Leu Tyr Thr His Thr Asn Asn Ser Arg Gly Ala Gly Arg
    50                  55                  60

Arg Leu Asp Gln Leu His Ile Ser Lys Ser Ser His His Ala Val Gln
65                  70                  75                  80

Phe Val Phe Asn Phe
                85

<210> SEQ ID NO 16
<211> LENGTH: 85
<212> TYPE: PRT
<213> ORGANISM: N. crassa

<400> SEQUENCE: 16

Gln Leu Lys Ile Leu Tyr Trp Asn Val Gly Lys Ser Tyr Asp Ile Val
1               5                   10                  15

Ala Ile Gln Glu Pro Gly Thr Thr Val Tyr Ser Ile Tyr Ser Pro Ile
            20                  25                  30

Leu Thr Asn Leu Val Ala Val Gly Asp Leu Asn Leu His His Pro Asp
        35                  40                  45

Trp Asp Pro Thr Arg Leu Gly Asn Ala Thr Arg Gly Glu Arg Asp Gly
    50                  55                  60

Thr Ile Asp His Ala Trp Leu Ser Gly Ser Asp His Cys Pro Gln Glu
65                  70                  75                  80
```

```
Ile Trp Val Gln Val
            85

<210> SEQ ID NO 17
<211> LENGTH: 36
<212> TYPE: PRT
<213> ORGANISM: Monascus BCR38072
<220> FEATURE:
<221> NAME/KEY: misc_feature
<222> LOCATION: (23)..(23)
<223> OTHER INFORMATION: Xaa can be any naturally occurring amino acid

<400> SEQUENCE: 17

Met Val Val Ala Ala Tyr Lys Ala Ser Phe Cys Tyr Ala Asp Asp Leu
1               5                   10                  15

Gly Ile Leu Phe Val Gly Xaa Ala Ala Asp Ser Leu Gln Glu Thr Ser
            20                  25                  30

Gln Gln Leu Val
        35

<210> SEQ ID NO 18
<211> LENGTH: 36
<212> TYPE: PRT
<213> ORGANISM: Monascus pilosus BCRC31502
<220> FEATURE:
<221> NAME/KEY: misc_feature
<222> LOCATION: (23)..(23)
<223> OTHER INFORMATION: Xaa can be any naturally occurring amino acid

<400> SEQUENCE: 18

Met Val Val Ala Ala Tyr Lys Ala Ser Phe Cys Tyr Ala Asp Asp Leu
1               5                   10                  15

Gly Ile Leu Phe Val Gly Xaa Ala Ala Asp Ser Leu Gln Glu Thr Ser
            20                  25                  30

Gln Gln Leu Val
        35

<210> SEQ ID NO 19
<211> LENGTH: 36
<212> TYPE: PRT
<213> ORGANISM: N. crassa
<220> FEATURE:
<221> NAME/KEY: misc_feature
<222> LOCATION: (23)..(23)
<223> OTHER INFORMATION: Xaa can be any naturally occurring amino acid

<400> SEQUENCE: 19

Leu Ala Thr Ile Pro Asn Thr Ile Thr Val Gly Phe Ala Asp Asp Thr
1               5                   10                  15

Asn Val Val Ala Val Ala Xaa Ala Ala Arg Thr Thr Glu Glu Asn Cys
            20                  25                  30

Arg Thr Leu Gln
        35

<210> SEQ ID NO 20
<211> LENGTH: 34
<212> TYPE: PRT
<213> ORGANISM: D. melanogaster

<400> SEQUENCE: 20

Lys Val Gly Asn Ala Ile Thr Asn Ala Ala Ala Phe Ala Asp Asp Leu
1               5                   10                  15

Val Leu Phe Ala Glu Thr Arg Met Gly Leu Gln Val Leu Leu Asp Lys
```

```
                20                  25                  30

Thr Leu

<210> SEQ ID NO 21
<211> LENGTH: 34
<212> TYPE: PRT
<213> ORGANISM: A. lumbricoides

<400> SEQUENCE: 21

Ala Gly Tyr Gly Phe Glu Ile Gly His Gln Phe Tyr Met Asp Asp Leu
1               5                   10                  15

Lys Leu Tyr Ala Arg Thr Pro Ala Met Leu Asp Ser Gln Ile Gln Val
            20                  25                  30

Val Ser

<210> SEQ ID NO 22
<211> LENGTH: 34
<212> TYPE: PRT
<213> ORGANISM: mouse L1

<400> SEQUENCE: 22

Gln Ile Gly Lys Glu Glu Val Lys Ile Ser Leu Leu Ala Asp Asp Met
1               5                   10                  15

Ile Val Tyr Ile Ser Asp Pro Lys Asn Ser Thr Arg Glu Leu Leu Asn
            20                  25                  30

Leu Ile

<210> SEQ ID NO 23
<211> LENGTH: 36
<212> TYPE: PRT
<213> ORGANISM: Y. lipolytica
<220> FEATURE:
<221> NAME/KEY: misc_feature
<222> LOCATION: (23)..(23)
<223> OTHER INFORMATION: Xaa can be any naturally occurring amino acid

<400> SEQUENCE: 23

Ala Val Ala Ala Gly His Met Lys Val Ser Ala Phe Ala Asp Asp Ile
1               5                   10                  15

Ala Val Phe Leu Asn Asn Xaa Ala Ala Ile Gln Asp Val Ala Thr Val
            20                  25                  30

Gly Arg Val Leu
        35

<210> SEQ ID NO 24
<211> LENGTH: 36
<212> TYPE: PRT
<213> ORGANISM: C. albicans
<220> FEATURE:
<221> NAME/KEY: misc_feature
<222> LOCATION: (23)..(23)
<223> OTHER INFORMATION: Xaa can be any naturally occurring amino acid

<400> SEQUENCE: 24

Val Asn Glu Val Ser Ser Val Ala Tyr Thr Ala Tyr Ala Asp Asp Val
1               5                   10                  15

Ile Ile Phe Phe Lys Asn Xaa Ala Ala Lys Asn Asp Gln Glu Arg Ile
            20                  25                  30

Gln Gln Leu Leu
        35
```

```
<210> SEQ ID NO 25
<211> LENGTH: 26
<212> TYPE: PRT
<213> ORGANISM: Monascus pilosus BCR38072

<400> SEQUENCE: 25

Arg Val Ser Trp Val Pro Gly His Thr Gly Ile Ala Gly Asn Glu Leu
1               5                   10                  15

Ala Asp Arg Leu Ala Lys Gln Gly Ala Ala
            20                  25

<210> SEQ ID NO 26
<211> LENGTH: 26
<212> TYPE: PRT
<213> ORGANISM: Monascus pilosus BCRC31502

<400> SEQUENCE: 26

Arg Val Ser Trp Val Pro Gly His Thr Gly Ile Ala Gly Asn Glu Leu
1               5                   10                  15

Ala Asp Arg Leu Ala Lys Gln Gly Ala Ala
            20                  25

<210> SEQ ID NO 27
<211> LENGTH: 26
<212> TYPE: PRT
<213> ORGANISM: C. gloeosporioides

<400> SEQUENCE: 27

Gln Thr His Trp Ser Pro Gly His Gln Gly Ile Lys Gly Asn Glu Glu
1               5                   10                  15

Ala Asp Ile Leu Ala Lys Glu Gly Thr Thr
            20                  25

<210> SEQ ID NO 28
<211> LENGTH: 26
<212> TYPE: PRT
<213> ORGANISM: S. cerevisiae

<400> SEQUENCE: 28

Gln Ile Glu Trp Val Lys Gly His Asp Gly Asp Pro Gly Asn Glu Met
1               5                   10                  15

Ala Asp Phe Leu Ala Lys Lys Gly Ala Ser
            20                  25

<210> SEQ ID NO 29
<211> LENGTH: 18
<212> TYPE: PRT
<213> ORGANISM: Monascus pilosus BCR38072

<400> SEQUENCE: 29

Ala Thr Cys Ser Cys Lys Lys Leu Lys Thr Pro Val His Phe Phe Phe
1               5                   10                  15

Cys Pro

<210> SEQ ID NO 30
<211> LENGTH: 18
<212> TYPE: PRT
<213> ORGANISM: Monascus pilosus BCRC31502

<400> SEQUENCE: 30

Ala Thr Cys Ser Cys Lys Lys Leu Lys Thr Pro Val His Phe Phe Phe
1               5                   10                  15
```

Cys Pro

<210> SEQ ID NO 31
<211> LENGTH: 18
<212> TYPE: PRT
<213> ORGANISM: mouse L1

<400> SEQUENCE: 31

Cys Trp Arg Gly Cys Gly Glu Arg Gly Thr Leu Leu His Cys Trp Trp
1               5                   10                  15

Glu Cys

<210> SEQ ID NO 32
<211> LENGTH: 18
<212> TYPE: PRT
<213> ORGANISM: D. melanogaster

<400> SEQUENCE: 32

Cys Arg Ala Gly Cys Asp Ala Pro Glu Thr Thr Asn His Ile Met Gln
1               5                   10                  15

Lys Cys

<210> SEQ ID NO 33
<211> LENGTH: 18
<212> TYPE: PRT
<213> ORGANISM: A. lumbricoides

<400> SEQUENCE: 33

Cys Arg Cys Cys His Ala Ala Pro Glu Thr Ala Glu His Ile Thr Ser
1               5                   10                  15

Ala Cys

<210> SEQ ID NO 34
<211> LENGTH: 20
<212> TYPE: PRT
<213> ORGANISM: N. crassa
<220> FEATURE:
<221> NAME/KEY: misc_feature
<222> LOCATION: (1)..(1)
<223> OTHER INFORMATION: Xaa can be any naturally occurring amino acid

<400> SEQUENCE: 34

Xaa Ala Ala Cys Ala Cys Gly Leu Glu Lys Glu Thr Phe Ala His Ile
1               5                   10                  15

Val Leu Asn Cys
            20

<210> SEQ ID NO 35
<211> LENGTH: 18
<212> TYPE: PRT
<213> ORGANISM: Y. lipolytica

<400> SEQUENCE: 35

Cys Gly Leu Cys Asp Lys Ala Ile Ile Gln Asp Leu His Glu His Ile
1               5                   10                  15

Phe Cys

<210> SEQ ID NO 36
<211> LENGTH: 18
<212> TYPE: PRT
<213> ORGANISM: C. albicans

<400> SEQUENCE: 36

-continued

```
Cys Gln Leu Cys Asn Thr Gly Thr Asp Ser Ile Val His His Ile Phe
1               5                   10                  15
Glu Cys
```

FUNGI NON-LTR RETROTRANSPOSONS AND METHODS RELATED THERETO

BACKGROUND

The invention relates to molecular biology and microbiology, and more particularly, to fungi retrotransposons.

Retroelements are classified into different types as well as telomeres, group II introns, retrons, retroviruses, LTR retrotransposons, non-LTR retrotransposons and so on (Flavell, 1995). So far there are approximately 30 elements corresponding to LTR retrotransposons and non-LTR retrotransposons recognized in fungi (Daboussi and Capy, 2003). Some characterizations of LTR retrotransposons have gag gene encoded intracellular ribonucleoprotein particles (Shiba and Saigo, 1983), pr gene encoded protease, int gene encoded integrase, rt gene encoded reverse transcriptase and RNaseH such as Pyret (Nakayashiki et al., 2001) and MAGGY (Farman et al., 1996) from *Magnaporthe grisea*, REAL from *Alternaria alternate* (Kaneko et al., 2000) and Nht2 from *Nectria haematococca* (Shiflett et al., 2002). Some retroviruses contain env gene encoded envelope glycoprotein for virus particles entering a new cell besides using the same genes of LTR retrotransposons to achieve the same approach (Bénit et al., 2001). Then, non-LTR retrotransposons, also known as LINEs, have a significant feature of lacking long terminal repeats far from LTR retrotransposon such as Zorro from *Candida albicans* (Goodwin et al., 2001), Ylli from *Yarrowia lipolytica* (Casaregola et al., 2002) and marY2N from *Tricholoma matsutake* (Murata et al., 2001). Most of non-LTR retrotransposons have two open reading frames found in fungi. The first open reading frame is considered to be the gag gene containing cysteine-rich DNA binding domains, although the first open reading frame does not show a conserved protein sequence. The second open reading frame encodes several conserved domains including endonuclease, reverse transcriptase, RNaseH domains and zinc finger motifs. Phylogenetic comparisons of the protein sequences suggest that non-LTR retrotransposons are the ancestors of LTR retrotransposon (Malik et al., 1999). Moreover, the oldest non-LTR retrotransposons is encoded by a single open reading frame due to their simpler construction.

Non-LTR retrotransposons were recently classified into 11 clades described by Malik et al. (1999). The position of a new non-LTR retrotransposon can be clearly revealed by phylogenetic tree analysis. The phylogenetic tree construction is based on the strong conserved domain of reverse transcriptase. The endonuclease domain is not very strongly conserved, although it is also used to classify non-LTR retrotransposons. Furthermore, the evolution of non-LTR retrotransposon is usually based on vertical transmission (Malik et al., 1999), but Bov-B LINE is an exception by horizontal transfer (Kordiš and Gubenšek, 1998) since it is distributed in Squamata as well as in Ruminantia (Kordiš and Gubenšek 1999).

*Monascus* has been applied in the food industry for thousands of years in China. Recently, it has been found that *Monascus* produces several bioactive substances. These bioactive substances are mainly the secondary metabolites of *Monascus*, including substances for reducing hypertension, substances for anti-putrefaction of bacteria such as monascidin, anti-cancer substances, substances for lowering blood sugar, ergostatin, anti-oxidants, and inhibitors of cholesterol such as monacolin (Endo et al., 1986; Komagata et al., 1989). Therefore, *Monascus* has been valued as a functional health food in recent years. To date, only a little genetic information of *Monascus* is discovered, therefore, a need for the study of *Monascus* genetics is desirable.

SUMMARY

Since there was little genetic information in *Monascus*, a BAC library of *Monascus* was constructed to provide a tool for genetic investigation. Surprisingly a series of repetitive sequences which are denominated as MRT, *Monascus* Retrotransposon were discovered. The characterization of the non-LTR retrotransposon MRT, and the distribution and phylogeny of MRT in *Monascus* were analyzed, and the invention was accomplished.

An isolated DNA molecule is therefore provided, comprising a nucleotide sequence selected from a group consisting of: a) a nucleotide sequence of SEQ ID NO: 1, b) a nucleotide sequence sharing 95% similarity to SEQ ID NO: 1, c) a nucleotide sequence encoding a polypeptide of an amino acid sequence of SEQ ID NO: 2, and d) a nucleotide sequence which hybridizes to any of the aforementioned nucleotide sequences under stringent conditions. A retrotransposon comprising the above described DNA molecule is also provided. The retrotransposon can be integrated into the genome of a cell.

In addition, an isolated DNA molecule is provided, comprising a nucleotide sequence selected from a group consisting of: a) a nucleotide sequence of SEQ ID NO: 3, b) a nucleotide sequence sharing 95% similarity to SEQ ID NO: 3, c) a nucleotide sequence encoding a polypeptide of an amino acid sequence of SEQ ID NO: 4, and d) a nucleotide sequence which hybridizes to any of the aforementioned nucleotide sequences under stringent conditions. A retrotransposon comprising the above described DNA molecule is also provided. The retrotransposon can be integrated into the genome of a cell.

Moreover, a method of introducing a DNA molecule into the genome of a cell is provided. The method comprises introducing any of the aforementioned retrotransposon into a cell, wherein the retrotransposon comprises a nucleotide sequence encoding a desired protein located in the DNA molecule, and the retrotransposon integrates into the genome of the cell under suitable conditions. The cell can be filamentous fungi, particularly *Monascus* sp., more particularly *Monascus pilosus*, *Monascus ruber*, or *Monascus purpureus*, still more particularly BCRC 38072.

In another embodiment, a vector comprising any of the aforementioned retrotransposons is provided. The vector can be a shuttle vector, or an expression vector.

Furthermore, a DNA delivery system comprising the vector is provided.

A method of isolating a retrotransposon is also provided. The method comprises amplifying a DNA fragment from a sample by oligonucleotides of nucleotide sequences of SEQ ID NO: 5 and 6, and identifying the DNA fragment as a retrotransposon when the DNA fragment contains endonuclease, retrotranscriptase, RNaseH domains, and zinc finger motifs.

BRIEF DESCRIPTION OF THE DRAWINGS

Fungi non-LTR retrotransposons and methods related thereto can be more fully understood and further advantages become apparent when reference is made to the following description and the accompanying drawings in which.

Figure 1:
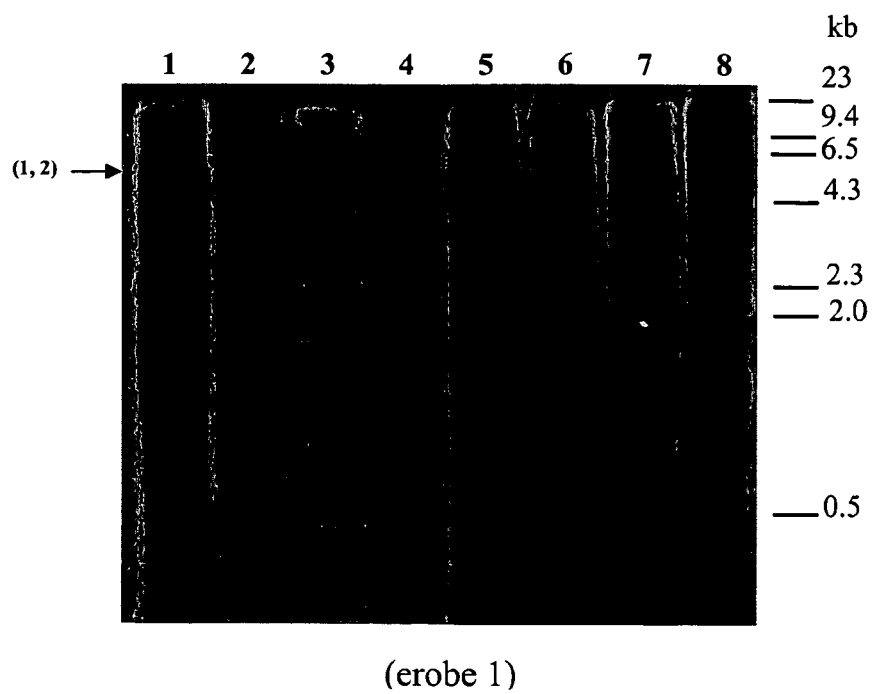
FIG. 1 shows southern hybridization analysis. Chromosome DNA extracted from *M. pilosus* BCRC38072 (lane 1), *M. purpureus* BCRC31542 (lane 2) and *M. purpureus*

BCRC31615 (lane 3), *M. kaoliang* BCRC31506 (lane 4), *M. pilosus* BCRC31502 (lane 5), *M. ruber* BCRC33323 (lane 6) and BCRC31523 (lane 7), and *M. sanguineus* BCRC33446 (lane 8) was digested by BamHI separated on electrophoresis gel and hybridized respectively with 420 bp probe1. (1, 2) was indicated for the predicted bands of MRT1 and MRT2.

Figure 2:
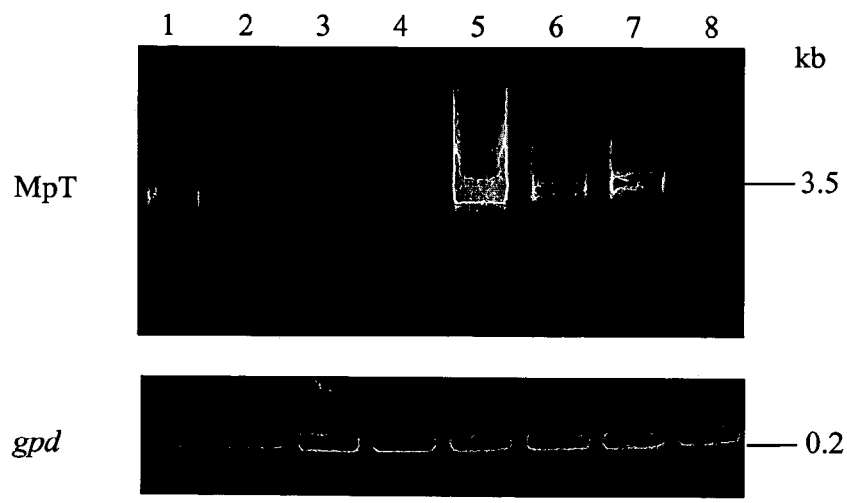

FIG. 2 shows comparative analysis of non-LTR retrotransposon (MRT) expression from various *Monascus* by RT-PCR. Total RNA was extracted from mycelium after 8 days of cultivation. Reverse transcriptase, primers and PCR kit described in Example 5 were used by RT-PCR. In each panel, lane 1 is *M. pilosus* BCRC38072, lane 2 is *M. purpureus* BCRC31542, lane 3 is *M. purpureus* BCRC31615, lane 4 is *M. kaoliang* BCRC31506, lane 5 is *M. pilosus* BCRC31502, lane 6 is *M. ruber* BCRC33323, lane 7 is *M. ruber* BCRC31523, and lane 8 is *M. sanguineus* BCRC33446. gpd gene indicates glyceraldehyde-3-phosphate dehydrogenase as control of RT-PCR.

FIG. 3A~3D show multiple alignment of deduced amino acid sequence of MRT sequence with related proteins from CgT1 (*C. gloeosporioides*), Tad1-1 (*N. crassa*), Zorro3 (*C. albicans*), Ylli (*Y. lipolytica*), L1Hs (human L1), L1Md (mouse L1), R2Dm (*D. melanogaster*), Dong (*B. mori*), R4 (*A. lumbricoides*) and RNaseH of yeast (*S. cerevisiae*). FIG. 3A shows comparison of the N-terminal apurinic/apyrimidinic endonuclease (APE) domain of Seq. ID No. 11-16. The putative endonuclease active sites are indicated by asterisks described by Feng et al. (1996). FIG. 3B shows comparison of the reverse transcriptase (RT) domain of Seq. ID No. 17-24. Conserved YXDD residues, active site of reverse transcriptase domain, are indicated above the alignment. FIG. 3C shows comparison of the RNaseH domain of Seq. ID No. 25-28. Conserved residues of RNaseH are described by He et al. (1996). FIG. 3D shows comparison of the C-terminal Cys-His region of Seq. ID No. 29-36. Conserved CX1CX7HX3C residues, putative zinc finger of MRT, are indicated above the alignment.

Figure 4:
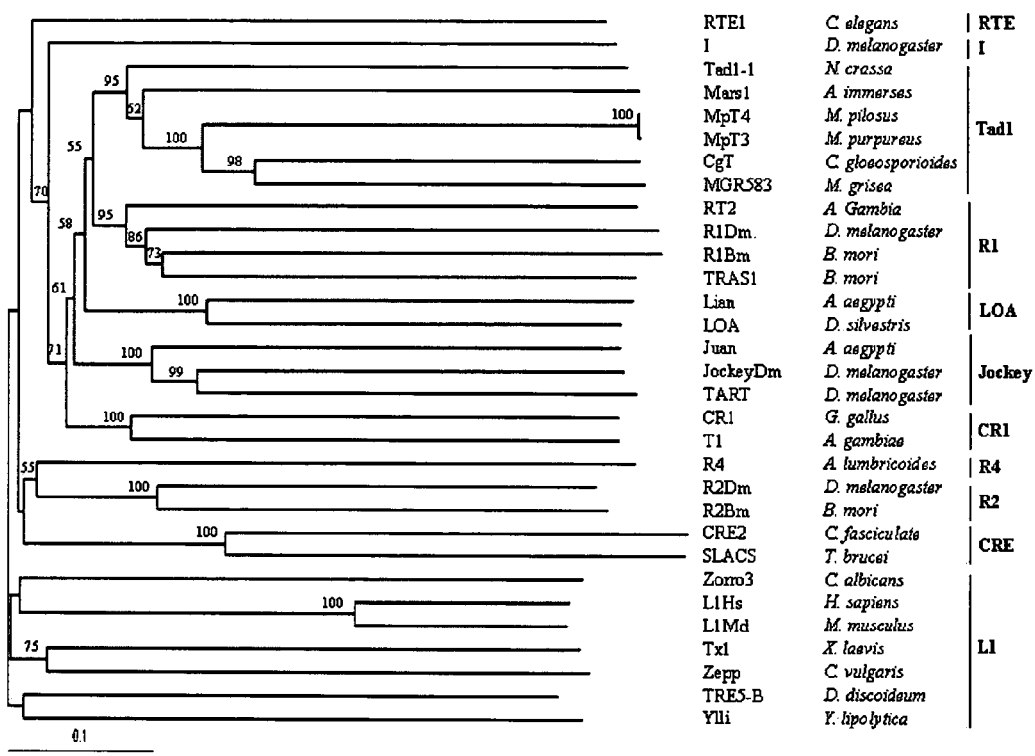

FIG. 4 shows phylogenetic tree of non-LTR retrotransposons from *Monascus* and various organisms. The phylogeny of non-LTR retrotransposons is based on the 11 conserved blocks of the reverse transcriptase domains defined by Malik et al. (1999). Bootstrap values are shown in the nodes according to the 100 replications. Only bootstrap values >50 are shown. The tree was constructed by the neighbor-joining method (Saitou and Nei, 1987).

DETAILED DESCRIPTION

Fungi non-LTR retrotransposons and methods related thereto are provided.

BAC mps01 clone was initially selected as containing a gene cluster involved in polyketide biosynthesis metabolism. Database searches and open reading frame prediction provided information on the putative gene loci and at least thirty ORFs were located within the BAC DNA. The BAC mps01 was completely sequenced with approximately 160 kb and the two repetitive sequences were observed and denominated as MRT1 and MRT2. The repetitive sequences were homology with CgT1 (He et al., 1996), a non-LTR retrotransposon, in *Colletotrichum gloeosporioides* (MRT1, 29% identity and MRT2, 30% identity) by BLASTX and contained no direct or inverted terminal repeats.

The BAC mps01 clone is derived from *Monascus* sp. BCRC38072. According to the classification system of Hawksworth & Pitt (1983), BCRC38072 was observed as having the characteristics of:

Macroscopic Characteristics:

CYA, 25° C., 7 days. Colonies 25-26 mm diam, mycelium white initially, becoming light reddish orange, reverse deep reddish orange.

MEA, 25° C., 7 days. Colonies 48 mm diam, bright reddish orange, reverse vivid reddish orange.

G25N, 25° C., 7 days. Colonies 28-29 mm diam, deep reddish orange, deep yellowish orange at the centers.

Microscopic Characteristics:

Aleurioconidia arising singly or occasionally in short chains, obpyriform to globose, 10-13×8-10 μm. Cleistothecia globose, 37-72 μm diam. Ascospores hyaline, ellipsoid, 4.6-6.3 (-6.6)×3.3-4.2 μm.

Accordingly, BCRC38072 was identified as:

Morphological Characteristics:

BCRC38072 is between *M. pilosus* and *M. rubber*.

1. BCRC38072 is similar to *M. pilosus* in colony color and growth rate.

2. BCRC38072 is similar to *M. ruber* in the morphology of ascospore.

Sequence Analysis:

BCRC38072, *M. ruber*, and *M pilosus* share 100% sequence similarity in rDNA ITS fragments and β-tubulin gene.

Species Identification:

BCRC38072 was temporarily denominated as *Monascus pilosus* K. Sato ex D. Hawksw. & Pitt.

It is not known whether MRT elements are uniquely exhibited in *M. pilosus* BCRC38072 or not. The genomic DNA of *M. pilosus* BCRC38072, *M. purpureus* BCRC31542, *M. purpureus* BCRC31615, *M. kaoliang* BCRC31506, *M. pilosus* BCRC31502, *M. ruber* BCRC33323, *M. ruber* BCRC31523, and *M. sanguineus* BCRC33446 was extracted and digested by BamHI to detect if the MRT elements were dispread in *Monascus*. Moreover, one set of oligonucleotide probes was designed according to the sequences of BAC mps01 clone. As shown in FIG. 1, MRT element was restricted in distribution within *M. pilosus* BCRC38072 and BCRC31502, *M. ruber* BCRC33323 and BCRC31523, and *M. sanguineus* BCRC33446, but there were a few bands individually displayed in *M. purpureus* BCRC31542, BCRC31615 and *M. kaoliang* BCRC31506. The fingerprint of DNA hybridization revealed that patterns of bands were distributed between 250 bp to 23 kb in *M. pilosus* BCRC38072 and BCRC31502, *M. ruber* BCRC33323 and BCRC31523, and *M. sanguineus* BCRC33446. In addition, there were at least 10 hybridizing bands with variable intensity exhibited in *M. pilosus* BCRC38072 and BCRC31502, *M. ruber* BCRC33323 and BCRC31523, and *M. sanguineus* BCRC33446, revealing a ladder of bands.

MRT1 and MRT2 non-LTR retrotransposons are degenerate elements. To determine whether there are active MRT non-LTR retrotransposons presented in *Monascus*, one set of oligonucleotide primers was designed for RT-PCR, which is required for transposition of non-LTR retrotransposons containing transcriptional activity. The result of RT-PCR is shown in FIG. 2. The predominant band of 3.5 kb displayed in *M. pilosus* BCRC38072 and BCRC31502, *M. ruber* BCRC33323 and BCRC31523 is the same with the expected size of MRT, but no expected band is seen in *M. purpureus* BCRC31542, BCRC31615, *M. kaoliang* BCRC31506, and *M. sanguineus* BCRC33446. Although the analysis of southern blot shows that MRT elements were exhibited in *M. purpureus* BCRC31542, BCRC31615, *M. kaoliang* BCRC31506, and *M. sanguineus* BCRC33446, they don't seem to be transcriptionally active. The predominant bands of 3.5 kb cDNA were further cloned into pGEM-T vectors for complete sequencing. The results show that MRT3 and MRT4 from *M. pilosus* BCRC38072 and BCRC31502 were full-length open reading frames without stop codons. MRT elements encode endonuclease, reverse transcriptase, RNaseH domains and zinc finger motif as shown in FIG. 3A~3D. It is probably that there are active MRT non-LTR retrotransposons presented in *M. pilosus* BCRC38072 and BCRC31502.

Reverse transcriptase domain is very strongly conserved and the 11 conserved block sequences of the reverse transcriptase domains defined by Malik et al. (1999) are widely used for construction of retrotransposon phylogeny. The result of phylogenetic tree indicates that the MRT retrotransposons are closer to the Tad1 clade (FIG. 4). MRT3 and MRT4 elements from *M. pilosus* BCRC38072 and BCRC31502 have very high homology, almost 100% identity. The MRT element was classified into the Tad1 clade including CgT1 from *C. gloeosporioides*, MGR583 from *Magnaporthe grisea*, Mars from *Ascobolus immerses*, Tad1-1 from *N. crassa* ($\geqq$40% similarity).

The data of southern blot analysis revealed that MRT element was displayed in different *Monascus* species. The results indicated that MRT element is stable exhibited in *Monascus*. The reason is probably the mechanism of non-LTR retrotransposon integration prevented from the evolution of horizontal transmission (Malik et al., 1999) and the MRT element has been evolving only for a short time.

The cDNA of MRT elements were obtained by RT-PCR and then cloned to the pGEM-T vector. The vector containing MRT3 is denominated as pGEMpT3 and deposited in Deutsche Sammlung Von Mikroorganismen und Zellkulturen GmbH (DSMZ) as DSMZ16979 on Dec. 13, 2004. Since MRT3 and MRT4 elements contain reverse transcriptase domains, reverse transcriptase enzymes can be produced by heterologous expression from the cDNA of the invention. The enzyme can be used as tools to carry out molecular technique of reverse transcription. In addition, MRT3 and MRT4 elements can be directly used as transposons for cell mutation or gene delivery as described in U.S. Pat. No. 6,150,160.

Accordingly, an isolated DNA molecule is provided, comprising a nucleotide sequence selected from a group consisting of: a) a nucleotide sequence of SEQ ID NO: 1 (MRT3 cDNA), b) a nucleotide sequence sharing 95% similarity to SEQ ID NO: 1, c) a nucleotide sequence encoding a polypeptide of an amino acid sequence of SEQ ID NO: 2, and d) a nucleotide sequence which hybridizes to any of the aforementioned nucleotide sequences under stringent conditions. The DNA molecule has two open reading frames without long terminal repeat. In some embodiments the DNA molecule has endonuclease, reverse transcriptase, RNaseH domains, and zinc finger motifs, especially reverse transcriptase domain. In addition, the DNA molecule is isolated from *Monascus*, particularly from *Monascus pilosus*, *Monascus ruber*, or *Monascus purpureus*, More particularly from BCRC38072.

In another embodiment, a retrotransposon comprising the above described DNA molecule is provided. The retrotransposon can be integrated into the genome of a cell.

In addition, an isolated DNA molecule is provided, comprising a nucleotide sequence selected from a group consisting of: a) a nucleotide sequence of SEQ ID NO: 3, b) a nucleotide sequence sharing 95% similarity to SEQ ID NO: 3, c) a nucleotide sequence encoding a polypeptide of an amino acid sequence of SEQ ID NO: 4, and d) a nucleotide sequence which hybridizes to any of the aforementioned nucleotide sequences under stringent conditions. The DNA molecule has two open reading frames without long terminal repeat. In some embodiments, the DNA molecule has endonuclease, reverse transcriptase, RNaseH domains, and zinc finger motifs, especially reverse transcriptase domain. In addition, the DNA molecule is isolated from *Monascus*, particularly from *Monascus pilosus*, More particularly from BCRC38072.

In another embodiment, a retrotransposon comprising the above described DNA molecule is provided. The retrotransposon can be integrated into the genome of a cell.

The phrase "hybridize under stringent conditions" means that positive hybridizing signal can be observed after heating at 42° C. in 6×SSC, 0.5% SDS and 50% formamide solution and washing 68° C. in 0.1×SSC, 0.5% SDS solution.

Moreover, a method of introducing a DNA molecule into the genome of a cell is provided. The method comprises introducing any of the aforementioned retrotransposons into a cell, wherein the retrotransposon comprises a nucleotide sequence encoding a desired protein located in the DNA molecule, and the retrotransposon integrates into the genome of the cell under suitable conditions. The cell can be filamentous fungi, particularly *Monascus* sp., more particularly *Monascus pilosus*, *Monascus ruber*, or *Monascus purpureus*, still more particularly BCRC 38072.

Furthermore, a vector comprising any of the aforementioned retrotransposons is provided. The vector can be a shuttle vector, or an expression vector. A DNA delivery system comprising the vector is also provided.

A method of isolating a retrotransposon is provided. An exemplary embodiment of the method comprises amplifying a DNA fragment from a sample by oligonucleotides of nucleotide sequences of SEQ ID NO: 5 and 6, and identifying the DNA fragment as a retrotransposon when the DNA fragment contains endonuclease, retrotranscriptase, RNaseH domains, and zinc finger motifs. It is easy for those skilled in the art to isolate or purify genes similar to non-LTR retrotransposons by known methods with the primers disclosed herein.

Practical examples are described herein.

EXAMPLES

Example 1

Strains and Incubation

*Monascus pilosus* BCRC38072 and BCRC31502, *Monascus purpureus* BCRC31542 and BCRC31615, *Monascus ruber* BCRC33323 and BCRC31523, *Monascus kaoliang* BCRC31506, and *Monascus sanguineus* BCRC33446 were used. The wild type strain BCRC38072 was used for a BAC library construction and DNA sequencing of the BAC clone. *M. purpureus* BCRC31542, *M. ruber* BCRC33323, *M. kaoliang* BCRC31506, *M. pilosus* BCRC31502, and *M. sanguineus* BCRC33446 were type strains. Fungi were grown in YM medium (DIFCO 271120) at 28° C. under 250 rpm flask shaking for 8 days.

Example 2

Nucleic Acid Manipulations

Fungal genomic DNA was isolated according to the method developed by Bingle et al. (1999). Colony hybridization and southern hybridization were performed using DIG system (Roch). One set of oligonucleotide primers (probe1: forward primer 5'-GGGGGGAAGCTAGGATATACGG-3' (SEQ ID NO: 5); reverse primer 5'-GCAGGTGGGTA-GAGCCACAG-3' (SEQ ID NO: 6)) was designed to carry out southern hybridization. All other DNA manipulations were performed as described in Sambrook et al. (1989).

Example 3

BAC Library Construction

The BAC library of *M. pilosus* BCRC38072 was constructed by the method developed by Peterson et al. (2000). pIndigoBAC-5 HindIII Ready (epicentre) vector was used for the construction of the BAC library. The competent cell (TransforMax™ EC 100™ electrocompent *Escherichia coli*, epicenter) was performed for the transformation by electroporation. When the transformants of the BAC library containing recombinant DNA were formed, the colonies were picked by Q-pix (Genetix) and preserved in the 384-well plates.

Example 4

Shotgun Genomic Sequencing and Assembly

The 3~5 µg BAC DNA (denominated as mps01) was sonicated and DNA fragments were blunted with Bal31 nuclease and T4 DNA polymerase. The 1~2 kb DNA fragments were recovered from an agarose gel after electrophoresis and inserted into pUC18/SmaI/CIAP (Pharmacia). The pUC18 vectors containing recombinant DNA were transformed into *E. coli* and transformants were picked by Q-pix (Genetix) and preserved in the 96-well plates. Ninety-six deep well plates were used to incubate the subclones and plasmids were high-throughput extracted. Cycle sequencing reactions were carried out using the BigDye v3.0 Kit with universal primer. DNA sequencing of 10 folds coverage and reaction kit were performed with ABI Prism 3700 Sequencer (Applied Biosystems). Phred-Phrap-Consed system developed by Phil Green laboratory was used to assemble DNA fragments.

Example 5 cDNA Analysis

The total RNA of *Monascus* was isolated by TRIzol reagent (Invitrogen) and the first strand cDNA was synthesized by ImProm-II™ Reverse Transcription System (Promega). One set of oligonucleotide primers (forward primer 5'-CATCATCCTGGTCCAAGAGCC-3' (SEQ ID NO: 7); reverse primer 5'-AGGTGAGAGGGGGAGC-CAGT-3' (SEQ ID NO: 8)) was designed to amplify cDNA of MRT with ExTaq PCR kit (Takara) and another set of oligonucleotide primers (forward primer 5'-ACGAGGCAT-CAATCCATCTC-3' (SEQ ID NO: 9); reverse primer 5'-CGTGGGTGCTGTCATACTTG-3' (SEQ ID NO: 10)) was designed to amplify partial cDNA of glyceraldehyde-3-phosphate dehydrogenase (gpd) for control of RT-PCR. The PCR products of cDNA were ligated with pGEM-T vector (Promega) and then several sets of oligonucleotide primers were designed for complete sequence of cDNA.

Example 6

Sequence Analysis

BLAST was used to screen sequence databases for homology. The complete BAC sequence data (mps01) were analyzed using Vector NTI 8.0 (InforMax). Phylogenetic tree was constructed by the neighbor-joining method (Saitou and Nei, 1987) and was presented by TreeView, Version 1.6.6, as shown in FIG. 4.

While the invention has been described by way of example and in terms of preferred embodiment, it is to be understood that the invention is not limited thereto.

REFERENCES

Bénit, L., Dessen, P., Heismann, T., 2001. Identification, phylogeny, and evolution of retroviral elements based on their envelope genes. J. Virol. 75, 11709-11719.

Bingle, L. E. H., Simpson, T. J., Lazarus, C. M., 1999. Ketosynthase domain probes identify two subclasses of fungal polyketide synthase genes. Fungal Genet. Biol. 26, 209-223.

Casaregola, S., Neuvéglise, C., Bon, E., Gaillardin, C., 2002. Ylli, a non-LTR retrotransposon L1 family in the dimorphic yeast *Yarrowia lipolytica*. Mol. Biol. Evol. 19, 664-677.

Daboussi, M. J., Capy, P., 2003. Transposable elements in filamentous fungi. Annu. Rev. Microbiol. 57, 275-299.

Endo, A., Komagata, D., Shimada, H., 1986. Monacolin M, a new inhibitor of cholesterol biosynthesis. J. Antibiot. (Tokyo). 39, 1670-1673.

Farman, M. L., Tosa, Y., Nitta, N., Leong, S. A., 1996. MAGGY, a retrotransposon in the genome of the rice blast fungus *Magnaporthe grisea*. Mol. Gen. Genet. 251, 665-674.

Feng, Q., Moran, J. V., Kazazian, H. H., Boeke, J. D., 1996. Human L1 retrotransposon encodes a conserved endonuclease required for retrotransposition. Cell, 87, 905-916.

Flavell, A. J., 1995. Retroelements, reverse transcriptase and evolution. Comp. Biochem. Physiol. 110, 3-15.

Goodwin, T. J., Ormandy, J. E., Poulter, R. T., 2001. L1-like non-LTR retrotransposons in the yeast *Candida albicans*. Curr. Genet. 39, 83-91.

He, C, Nourse, J. P., Kelemu, S., Irwin, J. A., Manners, J. M., 1996 CgT1: a non-LTR retrotransposon with restricted distribution in the fungal phytopathogen *Colletotrichum gloeosporioides*. Mol. Gen. Genet. 252, 320-331.

Kaneko, I., Tanaka, A., Tsuge, T., 2000. REAL, an LTR retrotransposon from the plant pathogenic fungus *Alternaria alternata*. Mol. Gen. Genet. 263, 625-634.

Komagata, D., Shimada, H., Murakawa, S., Endo, A., 1989. Biosynthesis of monacolins: conversion of monacolin L to monacolin J by a monooxygenase of *Monascus ruber*. J. Antibiot. (Tokyo). 42, 407-412.

Kordiš, D., Gubenšek, F., 1998. The Bov-B LINEs found in Vipers ammodytes toxic PLA2 genes are widespread in snake genomes. Toxicon. 36, 1585-1590.

Kordiš, D., Gubenšek, F., 1999. Molecular evolution of Bov-B LINEs in vertebrates. Gene. 238, 171-178.

Malik, H. S, Burke, W. D., Eickbush, T. H., 1999. The age and evolution of non-LTR retrotransposable elements. Mol. Biol. Evol. 16, 793-805.

Murata, H., Miyazaki, Y., Yamada, A., 2001. marY2N, a LINE-like non-long terminal repeat (non-LTR) retroelement from the ectomycorrhizal homobasidiomycete *Tricholoma matsutake*. Biosci. Biotechnol. Biochem. 65, 2301-2305.

Nakayashiki, H., Matsuo, H., Chuma, I., Ikeda, K., Betsuyaku, S., Kusaba, M., Tosa, Y., Mayama, S., 2001. Pyret, a Ty3/Gypsy retrotransposon in *Magnaporthe grisea* contains an extra domain between the nucleocapsid and protease domains. Nucleic Acids Res. 29, 4106-4113.

Peterson, D. G., Tomkins, J. P., Frisch, D. A., Wing, R. A., Paterson, A. H., 2000. Construction of plant bacterial artificial chromosome (BAC) libraries: An illustrated guide. Journal of Agricultural Genomics 5.

Saitou, N., Nei, M., 1987. The neighbor-joining method: a new method for reconstructing phylogenetic trees. Mol. Biol. Evol. 4, 406-425.

Sambrook, J., Fritsch, E., Maniatis, T., 1989. Molecular cloning: a laboratory manual. Cold Spring Harbor, Cold Spring Harbor Laboratory Press, New York.

Shiba, T., Saigo, K., 1983. Retrovirus-like particles containing RNA homologous to the transposable element copia in *Drosophila melanogaster*. Nature. 302, 119-124.

Shiflett, A. M., Enkerli, J., Covert, S. F., 2002. Nht2, a copia LTR retrotransposon from a conditionally dispensable chromosome in *Nectria haematococca*. Curr. Genet. 41, 99-106.

What is claimed is:

1. An isolated DNA molecule, comprising a nucleotide sequence selected from a group consisting of:
   a) a nucleotide sequence consisting of SEQ ID NO: 1; and
   b) a nucleotide sequence encoding a polypeptide consisting of the amino acid sequence of SEQ ID NO: 2.

2. The DNA molecule as claimed in claim 1, which has two open reading frames.

3. The DNA molecule as claimed in claim 1, which has no long terminal repeat.

4. The DNA molecule as claimed in claim 1, which encodes a polypeptide having reverse transcriptase activity.

5. The DNA molecule as claimed in claim 1, which encodes a polypeptide having endonuclease or RNaseH activity.

6. The DNA molecule as claimed in claim 1, which has zinc finger motifs.

7. The DNA molecule as claimed in claim 1, which is isolated from *Monascus sp.*

8. The DNA molecule as claimed in claim 1, which is isolated from *Monascus pilosus, Monascus ruber,* or *Monascus purpureus.*

9. A retrotransposon comprising the DNA molecule as claimed in claim 1, which has the ability of integrating into the genome of a cell.

10. A method of introducing a DNA molecule into the genome of a cell, comprising:
    introducing the retrotransposon as claimed in claim 9 into a cell, wherein the retrotransposon comprises a nucleotide sequence encoding a desired protein located in the DNA molecule, and the retrotransposon integrates into the genome of the cell under suitable conditions.

11. A vector comprising the retrotransposon as claimed in claim 9.

12. A DNA delivery system comprising the vector as claimed in claim 11.

* * * * *